United States Patent
Anastassiades

(10) Patent No.: US 6,479,469 B2
(45) Date of Patent: Nov. 12, 2002

(54) TREATMENT OF ARTHRITIS AND COMPOSITIONS THEREFORE

(76) Inventor: Tassos P. Anastassiades, 53 Kensington Avenue, Kingston, Ontario (CA), K7L 4B4

( * ) Notice: Subject to any disclaimer, the term of this patent is extended or adjusted under 35 U.S.C. 154(b) by 0 days.

(21) Appl. No.: 09/935,752

(22) Filed: Aug. 24, 2001

(65) Prior Publication Data
US 2002/0045597 A1 Apr. 18, 2002

(30) Foreign Application Priority Data
Aug. 29, 2000 (CA) .............................. 2317305

(51) Int. Cl.$^7$ .......................... A01N 43/04; A61K 31/70
(52) U.S. Cl. ........................................ 514/62; 536/55.2
(58) Field of Search .......................... 514/62; 536/18.7, 536/55.2, 825

(56) References Cited

U.S. PATENT DOCUMENTS

| | | |
|---|---|---|
| 3,697,652 A | 10/1972 | Rovati et al. |
| 4,314,999 A | 2/1982 | De Barbieri |
| 4,647,453 A | 3/1987 | Meisner |
| 4,710,491 A | 12/1987 | Lockhoff et al. |
| 5,030,721 A | 7/1991 | Kasai et al. |
| 5,696,098 A | 12/1997 | Muraki |

FOREIGN PATENT DOCUMENTS

| | | |
|---|---|---|
| EP | 0 309 411 | 3/1989 |
| EP | 0 356 275 B1 | 2/1990 |

OTHER PUBLICATIONS

Paulson, "Glycoproteins: what are the sugar chains for?", *TIBS*, Jul. 1989, pp. 272–276, vol. 14, Elsevier Science Publishers Ltd., UK.

Twoheed et al., "Glucosamine Therapy for Osteoarthritis", *Jnl. Of Rheumatology*, 1999, pp. 2294–2296, vol. 26:11.

Anastassiades, "Effect of a Synthetic Hexosamine Derivative on Mucopolysaccharide Synthesis by Human Capsule and Synovium", *Biochemical Pharmacology*, 1973, pp. 3013–3023, vol. 22, Pergamon Press, Great Britain.

Beekman et al., "Matris degradation by chondrocytes cultured in alginate: IL–1β induces proteoglycan degradation and proMMP synthesis but does not result in collagen degradation", *Osteoarthritis and Cartilage*, 1998, pp. 330–340, vol. 6:5, Osteoarthritis Research Society.

Kayser et al., "New amino sugar analogues are incorporated at different rates into glycoproteins of mouse organs", *Experientia*, 1993, pp. 885–887, vol. 49, Birkhäuser Verlag Basel.

Partridge et al., "Filter–paper Partition Chromatography of Sugars", *Biochem. J.*, 1948, pp. 238–250, vol. 42.

Chan et al., "Isolation and partial characterization of a high molecular weight anionic glycoconjugate from transforming growth factor–β treated bovine articular chondrocyte cultures", *Biochem. Cell Biol.*, 1996, pp. 233–240, vol. 74, Canada.

Howard et al., "Differential Effects of Bone Associated Factors on Newly Synthesized Anionic Glycoconjugates by Articular Chrondrocyte Cultures from Adult and Immature Bovines", *Jnl. Of Rheumatology*, 1993, pp. 2083–2094, vol. 20:12, Canada.

Brahn, Animal Models of Rheumatoid Arthritis:, *Clinical Orthopaedics and Related Research*, Apr. 1991, pp. 42–53, vol. 265.

Chen et al., "Oral Delivery of Group A Streptococcal Cell Walls Augments Circulating TGF–β and Suppresses Streptococcal Cell Wall Arthritis", *Jnl. Of Immunology*, 1998, pp. 6297–6304, vol. 161, American Association of Immunologists.

Lubineau, "Improved synthesis of glycosylamines and a straightforward preparation of N–acylglycosylamines as carbohydrate–based detergents", *Carbohydrate Research*, 1995, pp. 211–219, vol. 266, Elsevier Science B.V.

Ashcroft et al., "The effect of N–Acylglucosamines on the Biosynthesis and Secretion of Insulin in the Rat", *Biochem. J.*, 1976, pp. 701–707, vol. 154, Great Britain.

Johnson et al., "Lactose synthase: effect of α–lactalbumin on substrate activity of N–acylglucosamines", *Biophysica Acta*, 1985, pp. 373–377, vol. 832, Elsevier Science Publishers B.V.

Neuberger et al., "Inhibition of Lysozyme by N–Acyl–D––glucosamine Derivatives", *Nature*, Jul. 29, 1967, pp. 524–525, vol. 215.

Van Den Broek, et. al. Flare–up Reaction of Streptococcal Cell Wall Induced Arthritis in Lewis and F344 Rats: the Role of T Lymphocytes. *Clin. Exp. Immunol.*, vol. 79, 1990, pp. 297–306.

Talent, et. al. "Pilot Study of Oral Polymeric N–acetyl–D––glucosamine as a Potential Treatment for Patients with Osteoarthritis," *Clinical Therapeutics*, vol. 18, No. 6, 1996, pp. 1184–1190.

*Primary Examiner*—James O. Wilson
*Assistant Examiner*—Patrick Lewis
(74) *Attorney, Agent, or Firm*—Jeffrey S. Melcher; Manelli Denison & Selter, PLLC

(57) ABSTRACT

A 2-glucosamine derivative of the general formula (I):

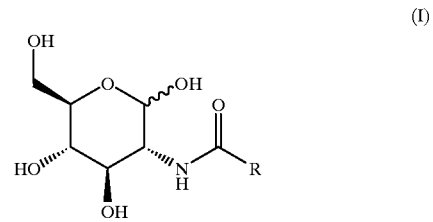

(I)

wherein R is an alkyl radical of the general formula $C_nH_{2n+1}$ and n is selected from 2–12; and pharmaceutically acceptable salts, esters and glucosides thereof, used for a treatment in a mammal selected from the group consisting of (a) arthritis, particularly osteoarthritis and inflammatory arthritis; (b) enhancing cartilage formation in a mammal; (c) enhancing chondrocytes cell proliferation; (d) production of glycosaminoglycan in a mammal; and (e) alleviating the symptoms of joint stiffness and restricted mobility.

15 Claims, 11 Drawing Sheets

TREATMENT OF ARTHRITIS AND COMPOSITIONS THEREFORE

FIELD OF THE INVENTION

This invention relates to N-acylated glucosamine derivatives; methods of treating arthritis, particularly osteoarthritis and inflammatory arthritis, enhancing cartilage formulation, enhancing chondrocyte cell proliferation and glycosaminoglycan production in a mammal with said derivatives; and pharmaceutical compositions comprising said N-acylated glucosamine derivatives.

BACKGROUND TO THE INVENTION

It is known that glycoconjugates play an important role in many biological processes. The carbohydrate groups confer important physical properties such as conformational stability, protease resistance, charge and water-binding capacity; and biological recognition, where sequence diversity provides signals for protein targeting and cell—cell interactions (Paulson 1989). The glycoconjugates of connective tissue matrices consist of hexosamines that are N-acetylated. However, the function of the N-acetyl moiety is not known.

The two major forms of arthritis in mammals are inflammatory arthritis, such as rheumatoid arthritis (RA), and osteoarthritis (OA), a progressive, degenerative loss of cartilage often secondary to mechanical stress, aging, dysplastic conditions and/or injury. Pain in OA is usually treated with NSAIDS (non-steroidal anti-inflammatory drugs). Inflammation and pain in RA is treated with NSAIDS, with new COX-2 inhibitors (also NSAIDS) and also with antimetabolites such as methotrexate. Other immunomodulators in clinical use or trials include interleukins and TNF receptor antagonists. Glucosamine is a popular non-prescription, neutraceutical treatment for pain in OA. Since RA and OA have different pathologies, it is not obvious that a treatment for one should result in a treatment for the other. A recent review, J. Rheumatol. (1999) 26:11-Anastassiades T., notes that many reports of glucosamine/OA clinical trials indicate positive findings but the mechanism of action is unknown.

When glucosamine is given even in very large doses to humans it is quickly cleared from circulation to the point that serum levels cannot be detected after oral or IV administration.

Glucosamine derivatives have been examined as potential therapeutic agents. When compared to glucosamine, N-acetylglucosamine (GluNac) has been shown to have a longer half-life when administered to humans Clin. Ther. (1996) 18:1184 in polyvalent or monvalent form, but no efficacy data were recorded. This reference proposes GluNac as a potential therapeutic for OA but it did not propose any rationale for therapy apart from serum levels.

A number of patents for example, U.S. Pat. No. 4,314,999, U.S. Pat. No. 5,696,098 and European Patent 356275 discuss chemical modifications of amino sugars that are structural components of oligosaccharides or polysaccharides i.e. covalently bound, but are not compounds of the present invention which are chemical modifications of a monosaccharide i.e. a single sugar molecule such as glucosamine.

Despite theories of chondroprotective actions, when given in vitro to bovine chondrocytes, glucosamine does not support growth or even survival of chondrocytes. In the presence of glucosamine, bovine chondrocytes grow much more slowly than in the absence of glucosamine, in culture which suggests it is not acting as a chondroprotective agent. Biochem. Pharmacol. (1973) 22:3018-Anastassiades T. discloses that a propionyl derivative of glucosamine actually inhibits the incorporation of labeled glucosamine into mucopolysaccharides, the older term for glycosaminoglycans and, accordingly, this reference teaches that N-propionyl glucosamine should inhibit cartilage formation.

Proteoglycan (PG) consists of a non-collagenous protein core to which long-chain polysaccharides (glycosaminogylcans, GAGs) are linked. PG is a key component of cartilage which accounts for its biomechanical properties. Type II collagen is the other principle component of cartilage. These two components are thus often used, alone or in combination, as in vitro surrogate markers for cartilage synthesis and degradation. Beekman R. (1998) Articular chondrocytes: synthesis and MMP-mediated degradation of extracellular matrix. Thesis from the Gaubius Laboratory of TNO Prevention and Health, Leiden, The Netherlands (ISN 90-9011354-1).

SUMMARY OF THE INVENTION

It is an object of the present invention to provide a method of treating arthritis, particularly, osteoarthritis, inflammatory arthritis, traumatic arthritis, degenerative arthritis and dysplastic arthritis.

It is a further object to provide a method of alleviating the unwanted symptoms of arthritis of joint stiffness and restricted mobility.

It is a further object to provide a method of enhancing cartilage formation.

It is a further object to provide a method of enhancing mammalian chondrocyte cell growth.

It is a further object to provide a method of enhancing the production of glycosaminoglycan in a mammal.

It is a further object to provide the use of N-acylated gluosamine derivatives for optimization of a bovine cartilage (BAC) growth assay for the stimulatory effects of these compounds. Accordingly, in one aspect the invention provides a method of treatment of arthritis, particularly, of osteoarthritis and inflammatory arthritis in a mammal comprising administering to said mammal an effective amount of a N-acylated-2-glucosamine derivative of the general formula (I):

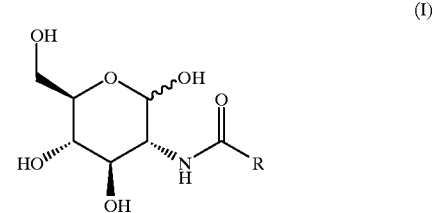

wherein R is an alkyl radical of the general formula $C_nH_{2n+1}$ wherein n is selected from 2–12, and pharmaceutically acceptable salts, esters and glucosides thereof.

Preferably, n is selected from 2–5 and more preferably 3.

In a further aspect the invention provides a method of enhancing chondrocyte cell proliferation comprising treating a population of chondrocyte cells with an effective amount of a N-acylated-2-glucosamine derivative as defined hereinabove.

In this specification, all references to glucosamine and its N-acylated derivatives means 2-amino-2-deoxy-D-glucose and its N-acylated derivatives (DGlcNs).

In this specification the term "mammals" includes, but is not limited to, human beings, particularly, dogs.

Specifically, the preferred compounds are:

N-Butyryl-D-glucosamine (2-n-Butanamido-2-deoxy-D-glucopyranose) (GlcNbu);

N-Valeryl-D-glucosamine (2-n-Pentanamido-2-deoxy-D-glucopyranose) (GlcNva);

N-Capryl-D-glucosamine (2-n-Hexanamido-2-deoxy-D-glucopyranose) (GlcNca) and branched alkyl isomers, e.g. secondary and tertiary analogues thereof.

The most preferred compound is N-butyryl-D-glucosamine, of the formula II:

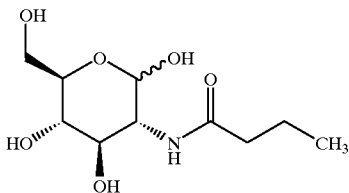

(II)

In a further aspect, the invention further provides a method for enhancing the production of glycosaminoglycan by the treatment of chondrocytes with an effective amount of a N-acylated-2-glucosamine as hereinabove defined.

In still a further aspect, the invention provides a method of enhancing cartilage growth and formation in a mammal by administering to said mammal an effective amount of a N-acylated glucosamine as hereinabove defined.

In yet a further aspect, the invention provides a diagnostic test involving the use of labeled N-derivitized glucosamine monomers to monitor growth of cartilage in subjects receiving treatment since the compounds of use in the present invention are incorporated into growing cartilage.

The N-acylated derivatives may be administered to a mammal by, for example, one of the following methods, namely, orally, intravenously, inter-arterially, dermally or subcutaneously.

The derivative may be typically administered in a suitable vehicle, in which the active ingredient is either dissolved or suspended in a liquid and which permits the N-acylated glucosamine to be delivered to the arthritic site from the bloodstream or transdermally. Solution compositions would be, typically, alcohol solutions, dimethyl sulfoxide solutions, or aqueous solutions containing, for example, polyethylene glycol. Such vehicles are well-known in the art, and useful for the purpose of delivering active ingredients to the site of action. To work, the active ingredient must be administered in a solvent that would prevent them from precipitating in the otherwise aqueous environment of the bloodstream. The solvent dimethylsulfoxide is one such solvent.

It will be understood by the person skilled in the art that the active N-acylated glucosamines as hereinbefore defined should be present in respective, effective amounts to (a) alleviate the symptoms of arthritis, (b) enhance cartilage formation in a mammal, (c) enhance chondrocyte cell proliferation, (d) enhance production of glycosaminoglycan; and (e) alleviate the symptoms associated with arthritis of joint stiffness and restricted mobility.

BRIEF DESCRIPTION OF THE DRAWINGS

In order that the invention may be better understood preferred embodiments will now be described by way of example only with reference to the accompanying drawings wherein:—

DETAILED DESCRIPTION OF PREFERRED EMBODIMENTS

Figure 1:
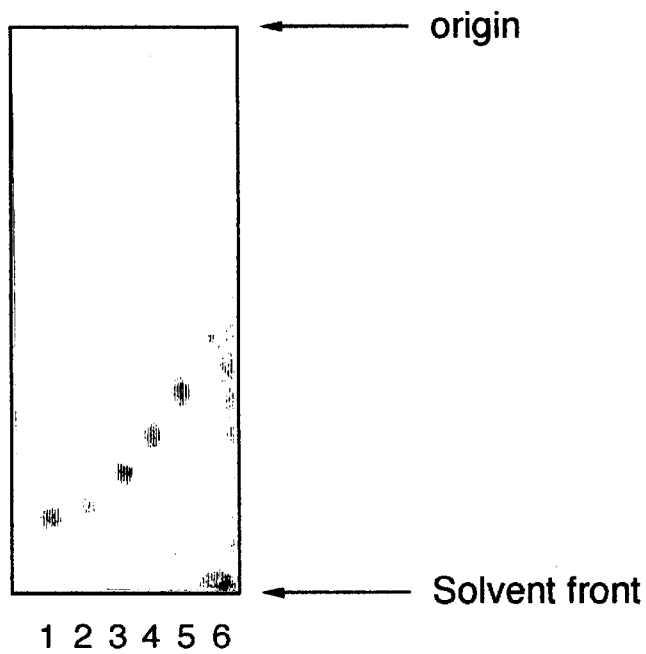
FIG. 1 is a chromatograph of DGlcNs on paper. DGlcNs were chromatographed on 3 mm Whatman paper using n-propanol/water/1 M sodium acetate pH 5 (7:2:1 v/v) solvent. The chromatograph was sprayed with acetylacetone and p-dimethylaminobenzaldehyde reagents, consecutively, and dried. Lane 1, GlcNca; lane 2, GlcNva; lane 3, GlcNbu; lane 4, GlcNpr; lane 5, GlcNac; lane 6, GlcN.

Experimental Methods
Synthesis of Hexosamine Derivatives.

The DGlcNs including N-acetylglucosamine (GlcNac), N-propionylglucosamine (GlcNpr), GlcNbu, N-valerylglucosamine (GlcNva) and N-caproylglucosamine (GlcNca) were synthesized according to modifications of the method previously described (Anastassiades T., Biochem Pharmacol 22:253–259, 1973), using glucosamine (GlcN) and/or [$^3$H]-GlcN and the respective carbonic acid anhydrides. The hexosamine derivatives were passed through cation-exchange resin to remove inorganic cations and any un-reacted glucosamine, lyophilized and stored in –20° C. freezer until use. Both a colour reaction and radioactivity from the parent [$^3$H]-GlCN were used to evaluate product formation and purification steps (Anastassiades T., Biochem Pharmacol 22:253–259, 1973). These derivatives were chromatographed on paper employing the method of Kayser et al (Experienta 49:885–887, 1993) and Partridge, S. M. (Biochem J 42:238–250, 1948).

Purification of N-Butyrylglucosamine (GlcNbu).

Lyophilized GlcNbu from the cation exchange column was reconstituted in about 3 ml of water and applied on water prewashed anion-exchange column (Amberlite IRA-400 OH; 1.5×30 cm). The column was washed with about 400 ml of water and thereafter eluted with magnesium chloride (MgCl$_2$) gradient (0.1–1.0 M) at the flow rate of 1 ml/3 min. Radioactivity in aliquots of 0.05 ml were determined. Radioactivity was measured in Rackbeta liquid scintillation counter (Fisher Scientific) after mixing aliquots of fractions with 5 ml of scintillation fluid (Ecolume, ICN). Conductivity of the column fractions was measured with the Cole Parmer conductivity meter (Chicago, USA). Column fractions corresponding to GlcNbu were pooled, lyophilized, and desalted on Bio-Gel P2 column.

The Amberlite IRA-400 resin in the hydroxide form was converted to the chloride form with a solution of sodium chloride. This was done by washing the resin overnight with 10% sodium chloride solution, followed with water for 2 d and the resin was kept in water until use. 3 ml of reconstituted sample was applied to water prewashed Bio-Gel P2 column. The column was initially eluted with water, followed with MgCl$_2$ gradient (0.05–0.5 M) at the flow rate of 1 ml/10 min. Column fractions corresponding to GlcNbu were pooled and lyophilized, followed by chromatography on Bio-Gel P2 column.

Reconstituted GlcNbu in water (2 ml) was applied to water prewashed Bio-Gel P2 column (1.5×70 cm). The column was eluted with water at the flow rate of 1 ml/10 min and the radioactivity of aliquots of the fractions were measured by liquid scintillation counting.

Synthesis of N-(2,4,5-Trihydroxy-6-hydroxymethyl-tetrahydro-pyran-3-yl)-butyramide (N-Butyryl glucosamine, GlcNBu) on a larger scale.

This method is based on a procedure by Inouye et al JACS 78,4722 (1956)

Glucosamine hydrochloride (20 g, 93 mmol) was added to a solution of methanol (anhydrous, 150 ml) and sodium methoxide (30 weight % solution in MeOH, 1 eq., 16.7 g 17.39 ml). The solution was mixed gently for 5 minutes and the resulting sodium chloride precipitate was filtered off by use of a fine sintered glass funnel. Butyric anhydride (1.2 equivalents, 111.6 mmol, 17.66 g =18.2 ml, from Aldrich Chemical Co, Ltd.) was then added in one portion with rapid stirring to the filtrate, after approximately 5 min the solution turbidified and precipitation of the product commenced. The reaction mixture was then stirred overnight. The reaction mixture was then cooled at 0° C. overnight. The crude N-butyryl glucosamine was then filtered and washed with a small portion of cold methanol, then a small portion of cold ethanol and finally by diethyl ether (200 ml). This crude material was then packed into a soxhlet extraction thimble and extracted with ethanol. Soxhlet extraction performed a thorough washing/recrystallization with >50% reduction of solvent volume. The ethanolic mixture of product was then cooled overnight in a cold room and the product was isolated by filtration. The product was washed with one small portion of cold ethanol followed by diethyl ether (50 ml). This gave GlcNBu as a pure white, crystaline powder in approx 80% overall yield. After freeze drying, the compound had a melting point of 212–213° C. (lit 212° C. Inouye).

Physical Characteristics:—

Melting point of 212–213° C. (lit 212° C. Inouye), uncorrected.

$^1$H NMR 200 MHz, (D$_2$O)δ(ppm); 5.02 d, ~0.5 H, β-anomeric H, J=3.4 Hz; 4.53, d, ~0.5H, α-amomeric H, J=8.1 Hz; 3.8–3.2, m, 6H, sugar—H, CH$_2$—OH; 2.1, td, 2H, CH$_3$CH$_2$CH$_2$—CO—, J=3.1 Hz, 6.9 Hz; 1.45, sextuplet, 2H, CH$_3$CH$_2$CH$_2$—CO—, J=6.9 Hz; 0.73, td, 3H, CH$_3$CH$_2$CH$_2$—CO—, J=1.5 Hz, 6.9 Hz.

HPLC: reverse phase HPLC, 250×4.6 mm (5 micron) LC8, 300 angstrom beads column. Mobile phase 50% MeOH/ 50% H$_2$O; flowrate 1.0 ml/min; uv detection @215 nm. Retention time of the two anomers of the product at 3.264 minutes and 3.407 minutes MS (mass spectrometry) by ES+ ionization. m/z; 288.2 (M+K$^+$), 272.1 (100%, M+Na$^+$), 250.2 (M+H$^+$).

The NMR and HPLC data showed the final product as obtained from the above reaction to be a mixture of α and β anomers in an approximate ratio of 1:1.

The following chemical structures denote preferred compounds and most preferred compounds of use in the practise of the invention.

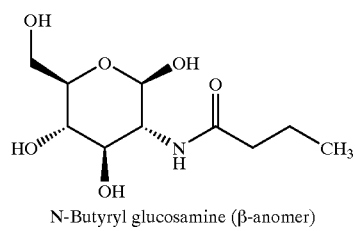

N-Butyryl glucosamine (β-anomer)

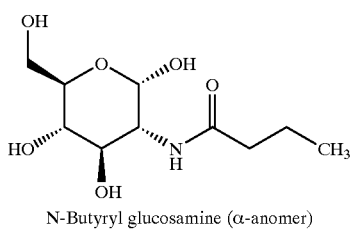

N-Butyryl glucosamine (α-anomer)

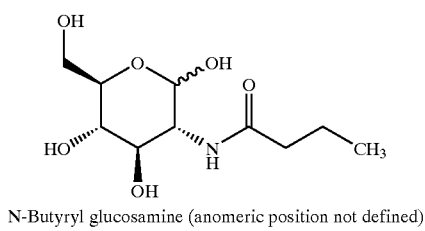

N-Butyryl glucosamine (anomeric position not defined)

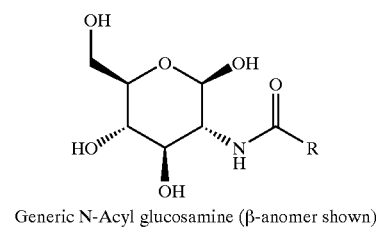

Generic N-Acyl glucosamine (β-anomer shown)

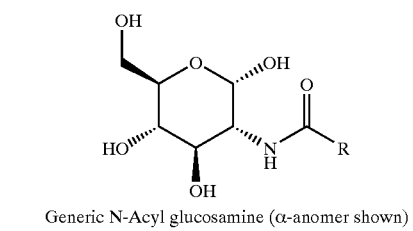

Generic N-Acyl glucosamine (α-anomer shown)

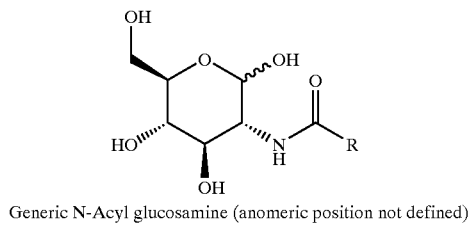

Generic N-Acyl glucosamine (anomeric position not defined)

The aforesaid compounds may be made according to the reaction schemes outlined hereinbelow, by way of examples for β-anomers and non-specific anomers.

Reaction scheme for N-Butyryl glucosamine (β-anomer indicated)

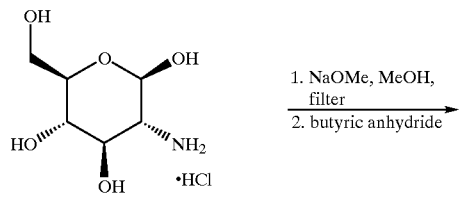

(II)

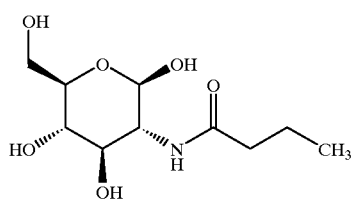

Reaction scheme for N-Butyryl glucosamine (anomeric position not defined)

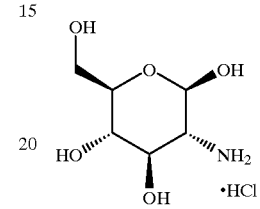
1. NaOMe, MeOH, filter
2. butyric anhydride

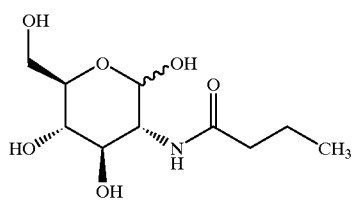

Reaction scheme for N-Acyl glucosamine (generic, R, β-anomer indicated)

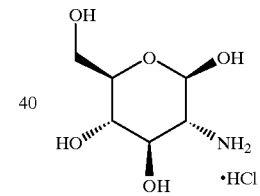
1. NaOMe, MeOH, filter
2. 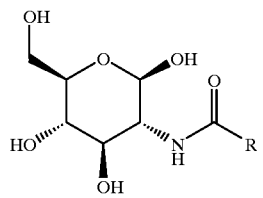

Reaction scheme for N-Acyl glucosamine (generic, R, anomeric position not defined)

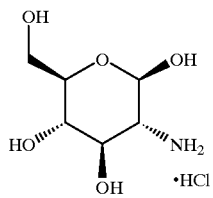
1. NaOMe, MeOH, filter
2. R

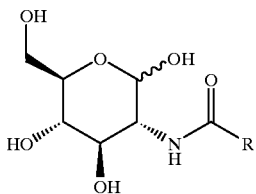

Paper Chromatography.

Five micro liters of reconstituted hexosamine derivative (100 μg/5 μl, in water was spotted on a Whatmann 3 MM paper, and descending paper chromatography was carried out as described by aforesaid Kayser et al (1993). The method of aforesaid Partridge (1948) was adapted to reveal the presence of glucosamine and hexosamine derivatives. For the determination of radioactivity, 1 inch cut paper strips from chromatograms were measured by scintillation counting.

Cell Culture.

Cartilage slices were removed aseptically from bovine knee joint and digested with collagenase to obtain single cell chondrocytes. Both primary cultures and subcultures were established by procedures described previously (Chan C. and Anastassiades T., Biochem Cell Biol 74:233–240, 1996; Howard S. and Anastassiades T., J Rheumatol 20:2083–2094, 1993).For the growth assays, cells were seeded at 15,000 cells/well and 33,000 cells/well for the 24 and 6 well plates, respectively, in glucose free Dulbecco's modified Eagle's culture medium, base which was supplemented with glucose (1 mg/ml) and serum (10%). These cells were incubated in a humidified atmosphere of 95% air and 5% carbon dioxide at 37° C. On the following day, the medium was changed to fresh medium containing test materials of interest. The cells were harvested at time intervals and cell number determined using Coulter counter (Coulter Electronics Inc. Florida, USA). Results are expressed as the means of three replicate wells and each well was counted twice. The data are presented as mean ± SEM.

Results and Discussion

Hexosamine derivatives.

There was 100% conversion of the parent hexosamine to DGlcN. The five different DGlcNs synthesized were analyzed by descending paper chromatographed. Two spots were observed on the chromatograms for each of the DGlcNs (FIG. 1). The upper major spot represents the derivative, while the lower minor one is an impurity. However, the DGlcNs migrate at different rates, depending on the length of the modified N-acyl side chain. GlcNca migrates faster than GlcNva, followed by GlcNbu, GlcNpr and GlcNac. The question arose on how best to purify acyl hexosamine from the minor contaminating product on a small preparative scale.

Figure 2:
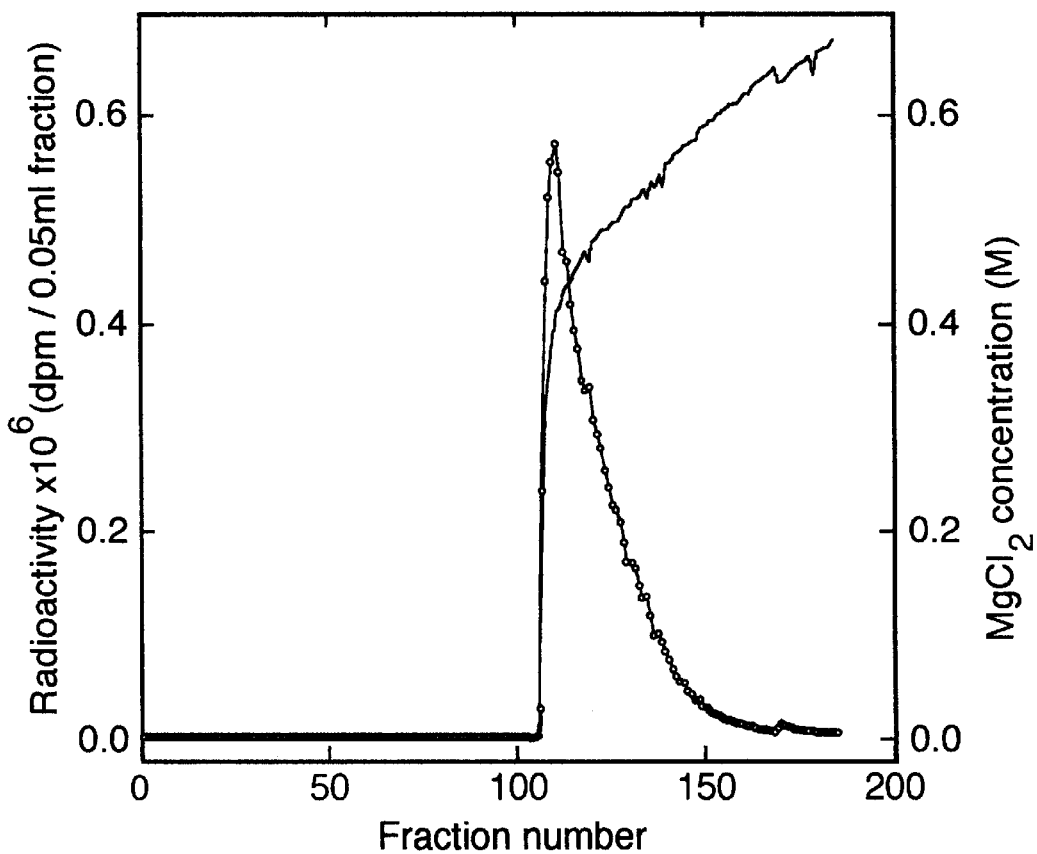
FIG. 2: Is an elution profile of GlcNbu, labelled with tritium on anion-exchange (amberlite IRA-400 OH) column. After cation-exchange, GlcNbu was loaded on water pre-washed column. The column was eluted with water followed by $MgCl_2$ gradient (0.1 –1 M) and 1 ml/3 min fractions were collected. O, $^3H$ Radioactivity, and ⁻, $MgCl_2$ concentration.
Figure 3:
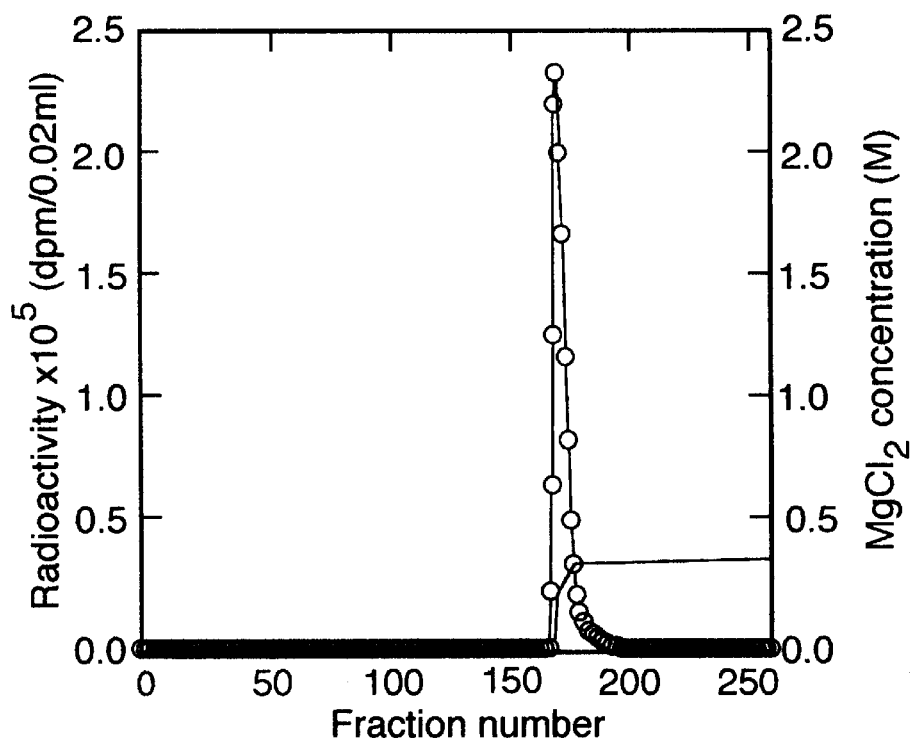
FIG. 3: Is an elution profile of GlcNbu on anion-exchange column (1.5×30 cm) with $MgCl_2$ gradient. Flow rate 1 ml/10 min. O, Radioactivity, and —, $MgCl_2$ concentration.
Figure 4:
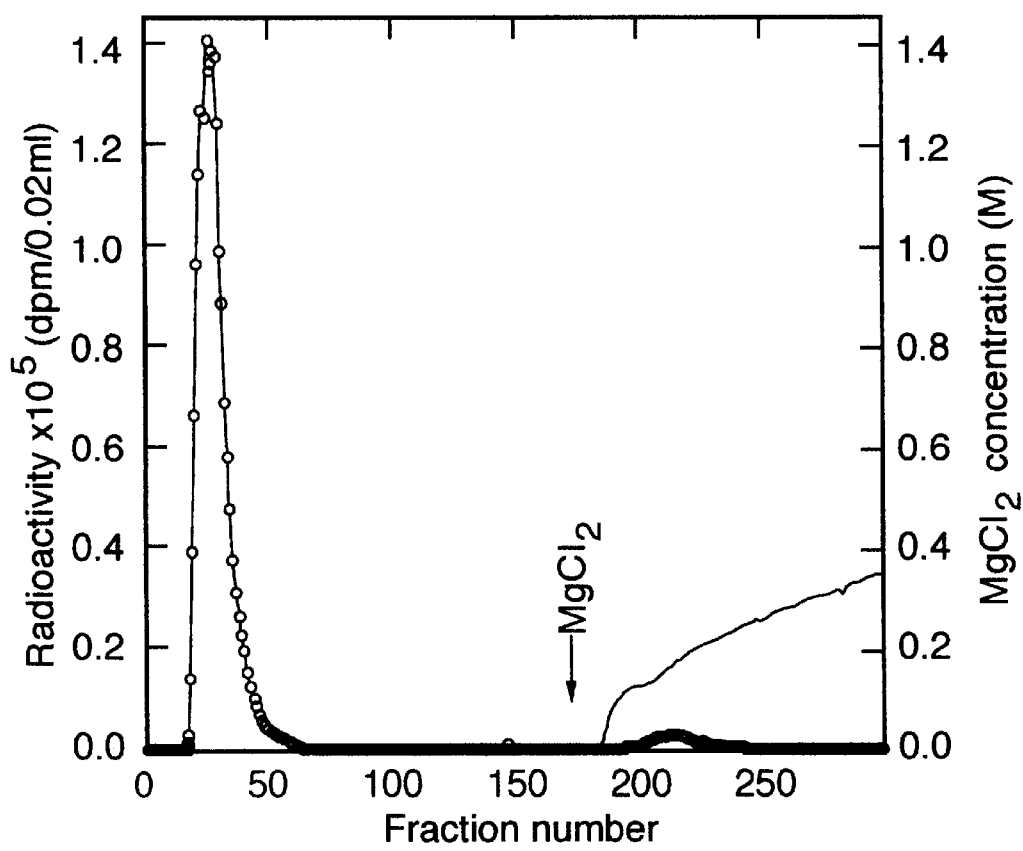
FIG. 4: Is the elution of GlcNbu on anion-exchange (Cl⁻) column with $MgCl_2$ gradient. O, Radioactivity, and —, $MgCl_2$ concentration.

Subsequent purification steps for GlcNbu were then evaluated. Initially, GlcNbu was eluted from anion-exchange (amberlite IRA-400 OH) column with $MgCl_2$ gradient (0.1–1.0 M) at the flow rate of 1 ml/3 min (FIG. 2). Elution of amorphous crystals in column fractions were observed before and during the elution of first few fractions of GlcNbu. Reduction of the flow rate to 1 ml/10 min in order to obtain better separation gave a similar pattern of elution (FIG. 3), but with an increase in amorphous crystal formation. In experiments to determine the effect of $MgCl_2$ concentration on GlcNbu purification, carried at a flow rate of 1 ml/10 min, profiles similar to that shown in FIG. 3 were observed when $MgCl_2$ gradient was water –0.5 M or 0.05–0.5 M (data not shown). The amorphous crystal were soluble in dilute hydrochloric acid and thus may be magnesium hydroxide that formed due to exchange of anions between $MgCl_2$ and the hydroxide form of the anion-exchange resin. In all the anion-exchange column, the $MgCl_2$ gradient curve was steep. When the hydroxyl group of the anoin-exhanger resin was replaced with the chloride form, GlcNbu did not bind to the column and hence was eluted with water (FIG. 4). A second peak was obtained when the column was eluted further with $MgCl_2$ gradient (0.05–0.5 M). The $MgCl_2$ concentration in column fractions increased gradually in the chloride form of the anion-exchange resin unlike abrupt increase exhibited by the hydroxide form. The chloride form of anion-exchange resin column is a useful step in the removal of the impurity from GlcNbu synthesized product with a relative ease by water elution. The impurity binds to an anion-exchange resin, while GlcNbu is eluted.

Figure 5A:
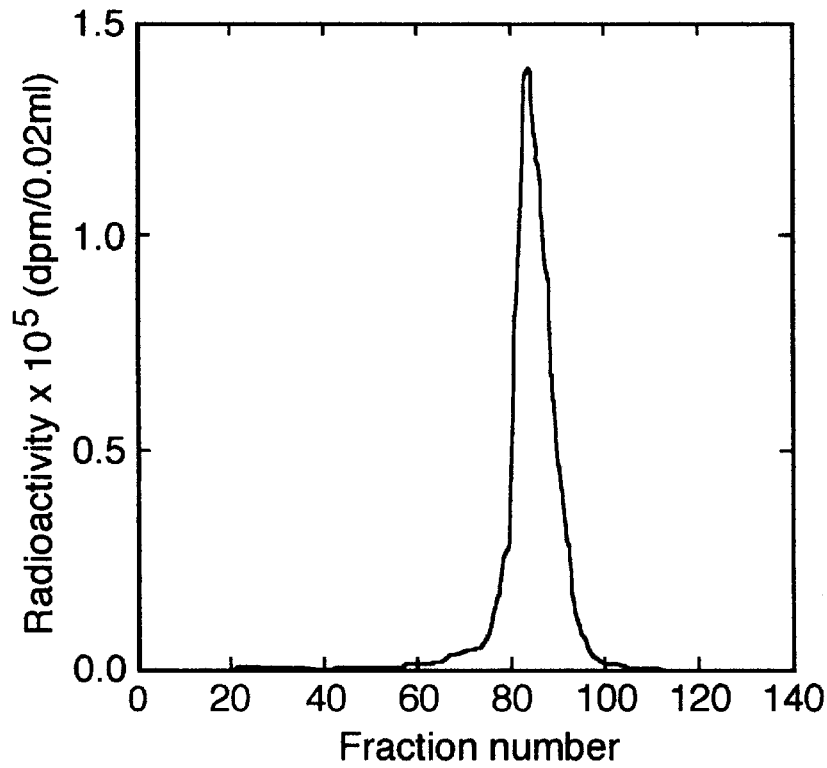
FIG. 5: The represents the Bio-Gel P2 column chromatography of lyophilized GlcNbu from (A) hydroxyl form of anion-exchange resin column, and (B) chloride form of anion-exchange resin column. GlcNbu is the major peak.
Figure 5B:
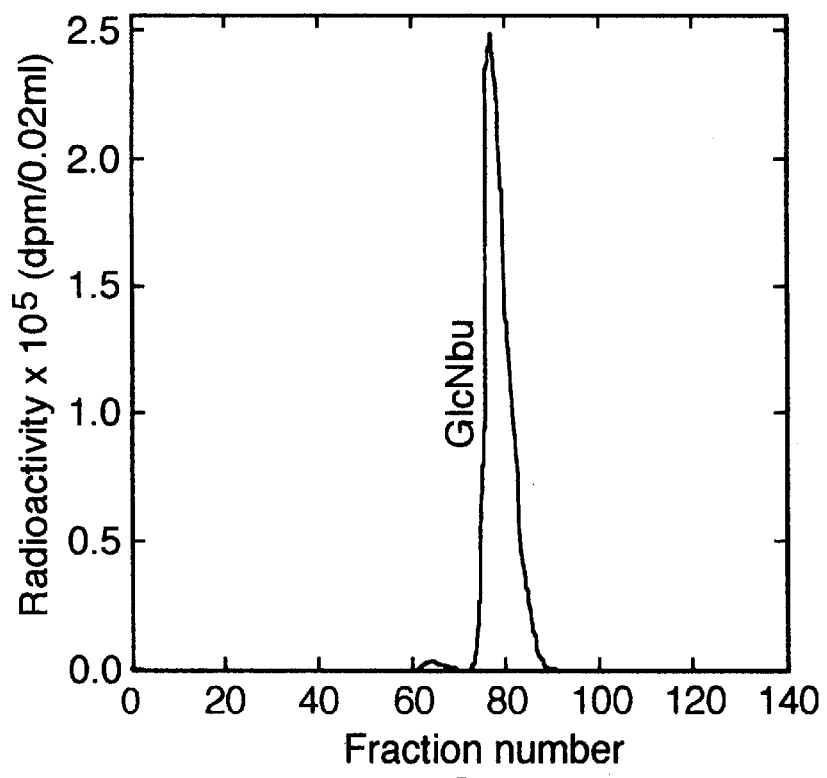

FIG. 5A shows the elution profile of GlcNbu (which was obtained from the hydroxide form of anion-exchange resin column) on Bio-Gel P2 column. GlcNbu purification on Bio-Gel P2 column, after the initial chloride form of anion-exchange step, gave a major peak (FIG. 5B). The yield of GlcNbu after anio-exchange, followed by Bio-Gel P2 chromatography is approximately 80%.

Figure 6:
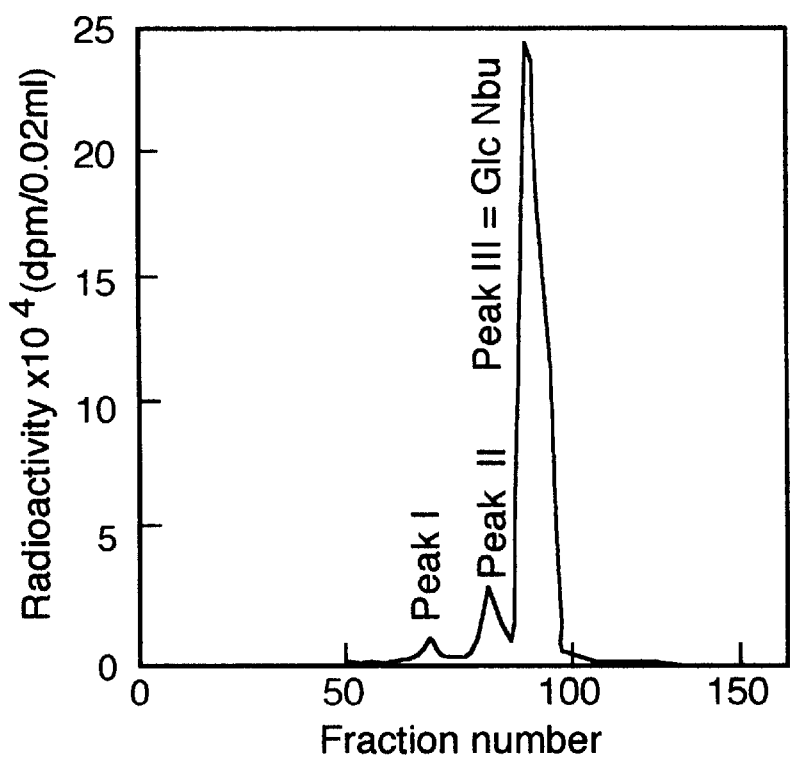
FIG. 6: This represents the purification of GlcNbu on Bio-Gel P2 column. The column was equilibrated and eluted with water. Flow rate 1 ml/10 min.
Figure 7A:
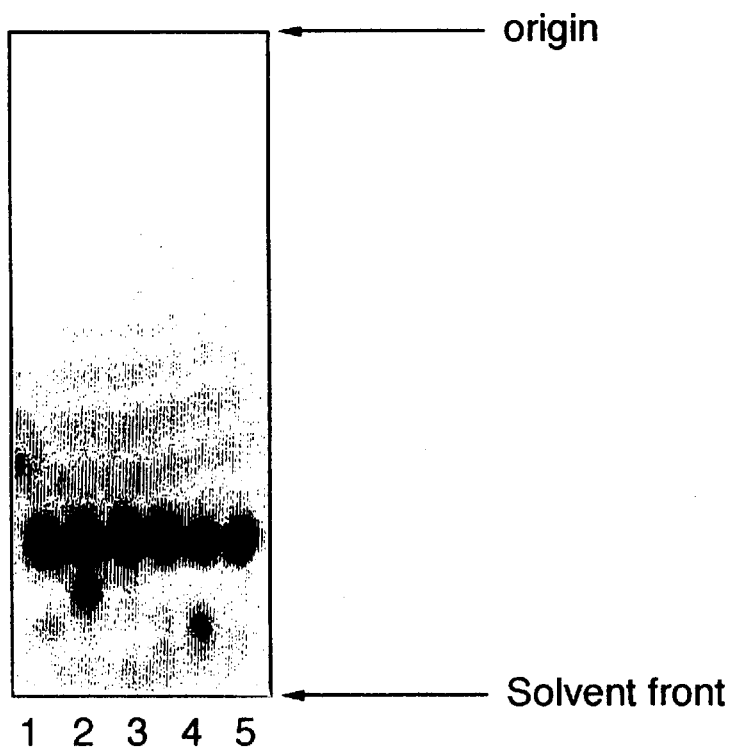
FIG. 7A: Is a photograph of GlcNbu purified samples chromatographed on paper. GlcNbu was chromatographed on paper, sprayed with acetylacetone and p-dimethylaminobenzaldehyde reagents consecutively. Lane 1, after cation-exchange; lane 2, anion-exchange (OH⁻) followed by Bio-Gel P2; lane 3, anion-exchange (Cl⁻) followed by Bio-Gel P2; lane 4, Bio-Gel P2; lane 5, after cation-exchange; and lane 6, Bio-Gel P2. GlcNbu samples in lanes 5 and 6 are non radioactive.
Figure 7B:
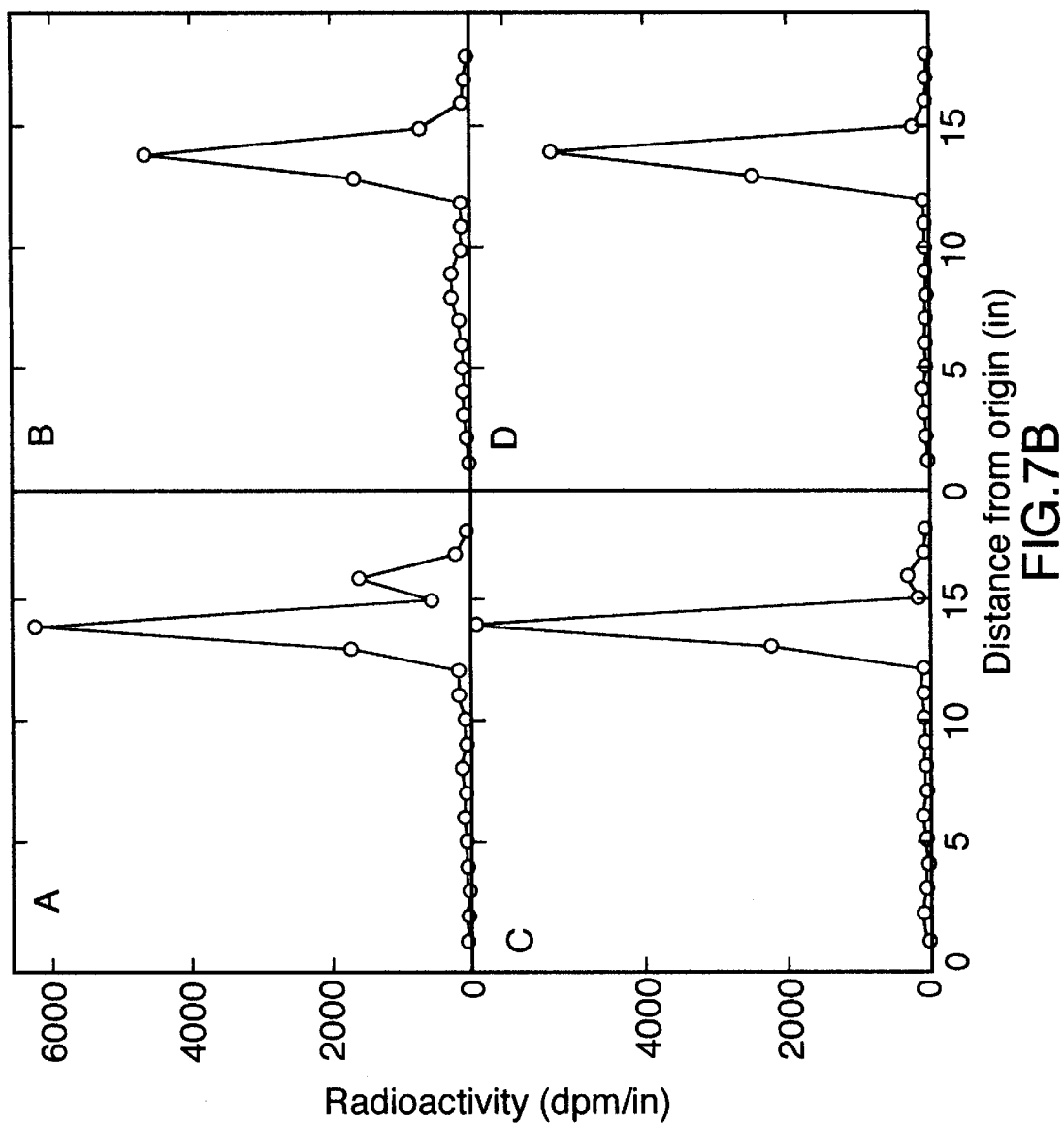
FIG. 7B: Is a chromatograph of GlcNbu samples. 1 inch sizes of the chromatograph paper for lanes 1–4 of FIG. 6A were cut starting from the origin and counted. A, GlcNbu obtained after anion-exchange chromatography; B, GlcNbu after anion-exchange (OH⁻) and Bio-Gel P2; C, anion-exchange (Cl⁻) followed by Bio-Gel P2; D, Bio-Gel P2.

Purification of GlcNbu using only Bio-Gel P2 column shows three peaks (FIG. 6). The third peak corresponds to GlcNbu with a yield of approximately 90%. The purity obtained with Bio-Gel P2 is as good as that obtained with the chloride form of anion-exchange resin. Results obtained from paper chromatography showed that Bio-Gel P2 column chromatography promises to be a better method of obtaining highly purified GlcNbu compared to anion-exchange chromatography (FIG. 7A and B). Therefore, Bio-Gel P2 column was also used to purify non-radioactive GlcNbu for cell growth assays (FIG. 7A).

Effects of DGlcNs on BAC Growth in Culture.

Figure 8:
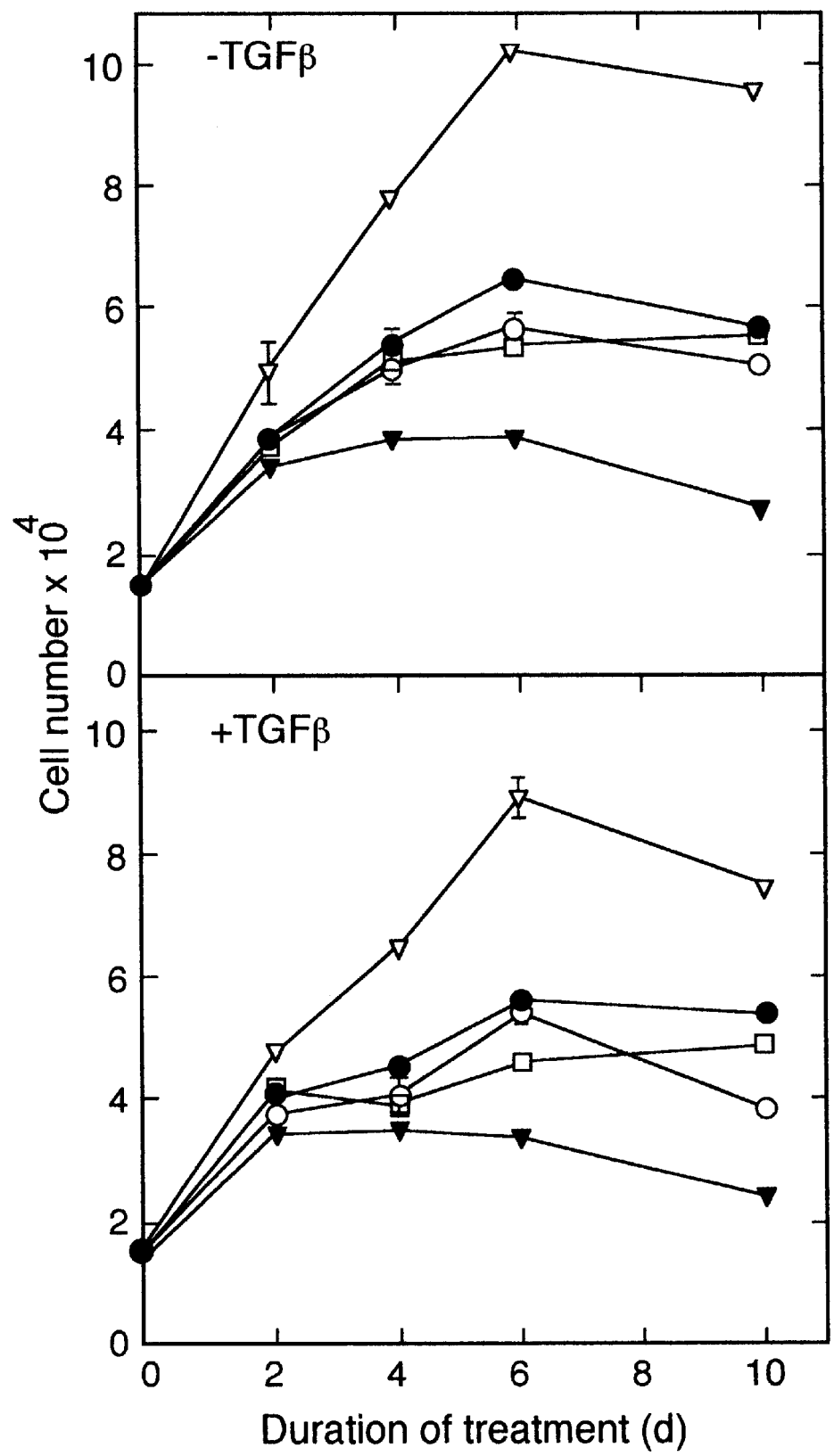
FIG. 8: This represents the effect of DGlcNs (1 mg/ml) on the proliferation of chondrocytes in the presence and absence of transforming growth-β (TGFβ; 10 μg/ml). BAC subculture 6 cells were treated with the respective test materials: □, Control; O, GlcNac; ●, GlcNpr; ∇, GlcNbu; and ▼, GlcN. The cells were harvested and counted at various time intervals (0–10 d).
Figure 9:
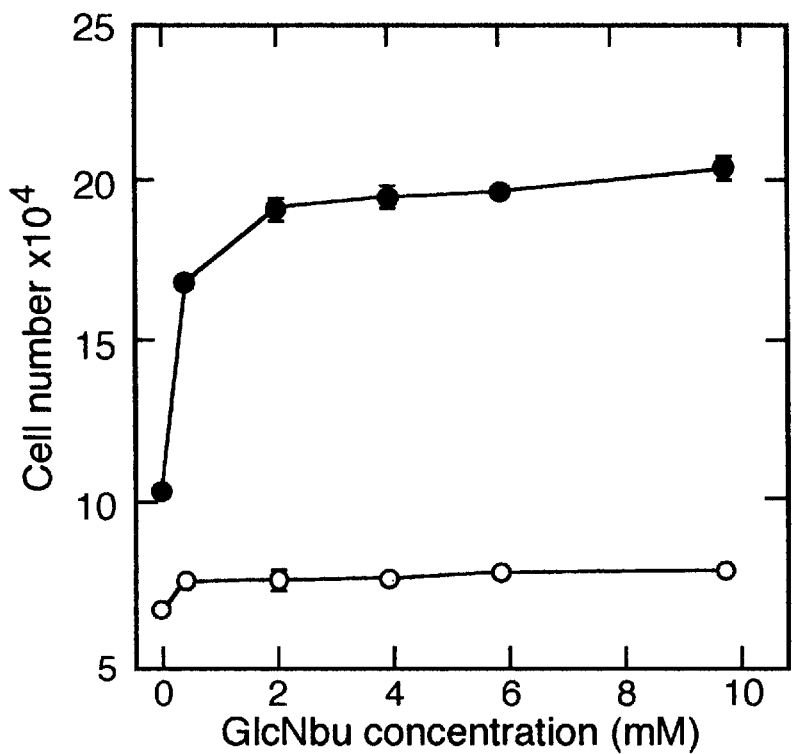
FIG. 9: This represents the effect of serum and GlcNbu on chondrocyte cell proliferation. BAC subculture 7 cells were treated for 7d with various GlcNbu concentrations at varying medium serum. Cell number represent final cell count at day 7. O, 10% serum, and ●, 20% serum.

Initial studies examined the effect of 1 mg/ml of GlcN, GlcNac, GlcNpr and GlcNbu on the proliferation of chondrocytes (BAC subculture 6) maintained in medium supplemented with glucose (0.5 mg/ml), TGF-β (10 μg/ml) and serum (10%). GlcNbu significantly stimulated cell growth, while GlcNac and GlcNpr had a much reduced effect on cell growth (FIG. 8). GlcN at the same concentration as the DGlcNs inhibited cell growth compared to control (FIG. 8). At various serum and GlcNbu (0.4–10 mM) concentrations, there was more increase in cell growth at 20% than 10% serum in the presence of GlcNbu and glucose (1 mg/ml) (FIG. 9). The cells barely thrive at serum concentrations lower than 10% (data not shown).

Figure 10:
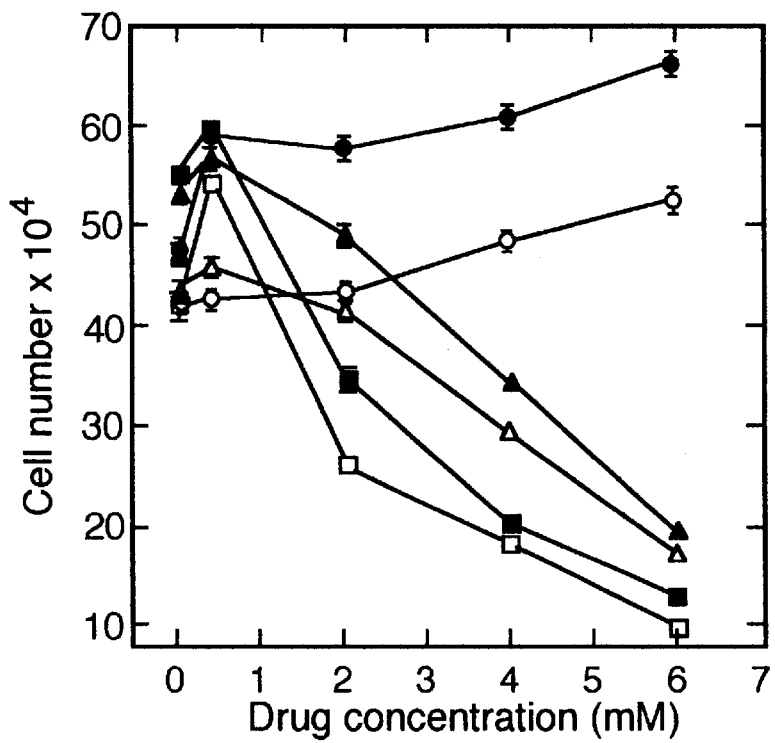
FIG. 10: This represents the effects of GlcNbu, GlcN and sodium butyrate on chondrocyte cell proliferation. BAC subculture 6 cells were treated for 6d and 12d with the designated drug, and cell were counted on those days. O, GlcNbu for 6d; ●, GlcNbu for 12d; ∇, GlcN for 6d; ▼, GlcN for 12d; □, ■ sodium butyrate for 6d; and ■ sodium butyrate for 12d.
Figure 11:
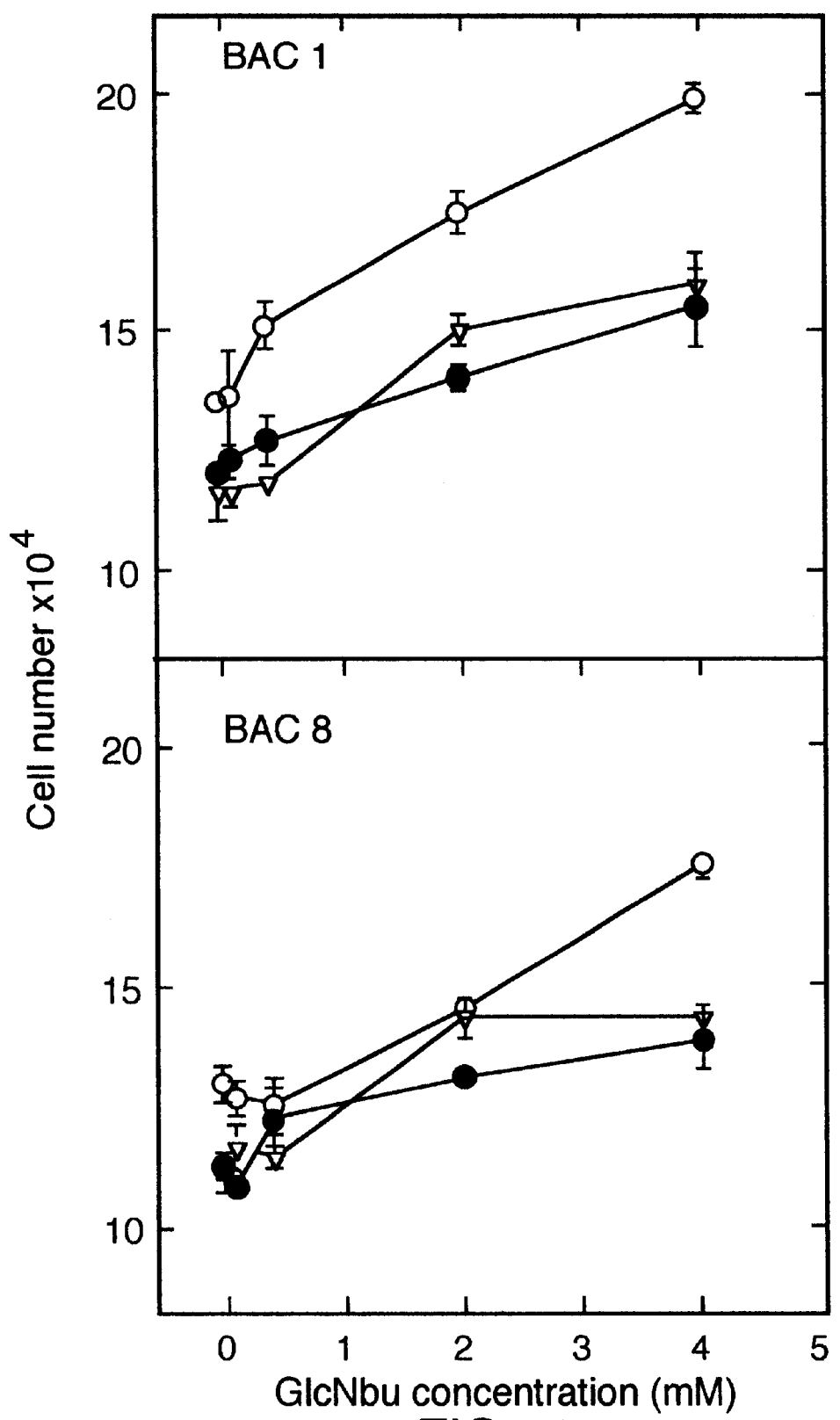
FIG. 11: This represents the effect of GlcNbu on chondrocyte cell proliferation at various medium glucose concentrations. Cultured cells were treated for 7d with the designated concentrations of GlcNbu and glucose, and cell number determined on day 7. The upper and lower panels represent cell numbers for early BAC subculture one and late subculture eight, respectively. O, 0.125 mg/ml glucose; ●, 0.25 mg/ml glucose; and ▽, 0.5 mg/ml glucose.
Figure 12:
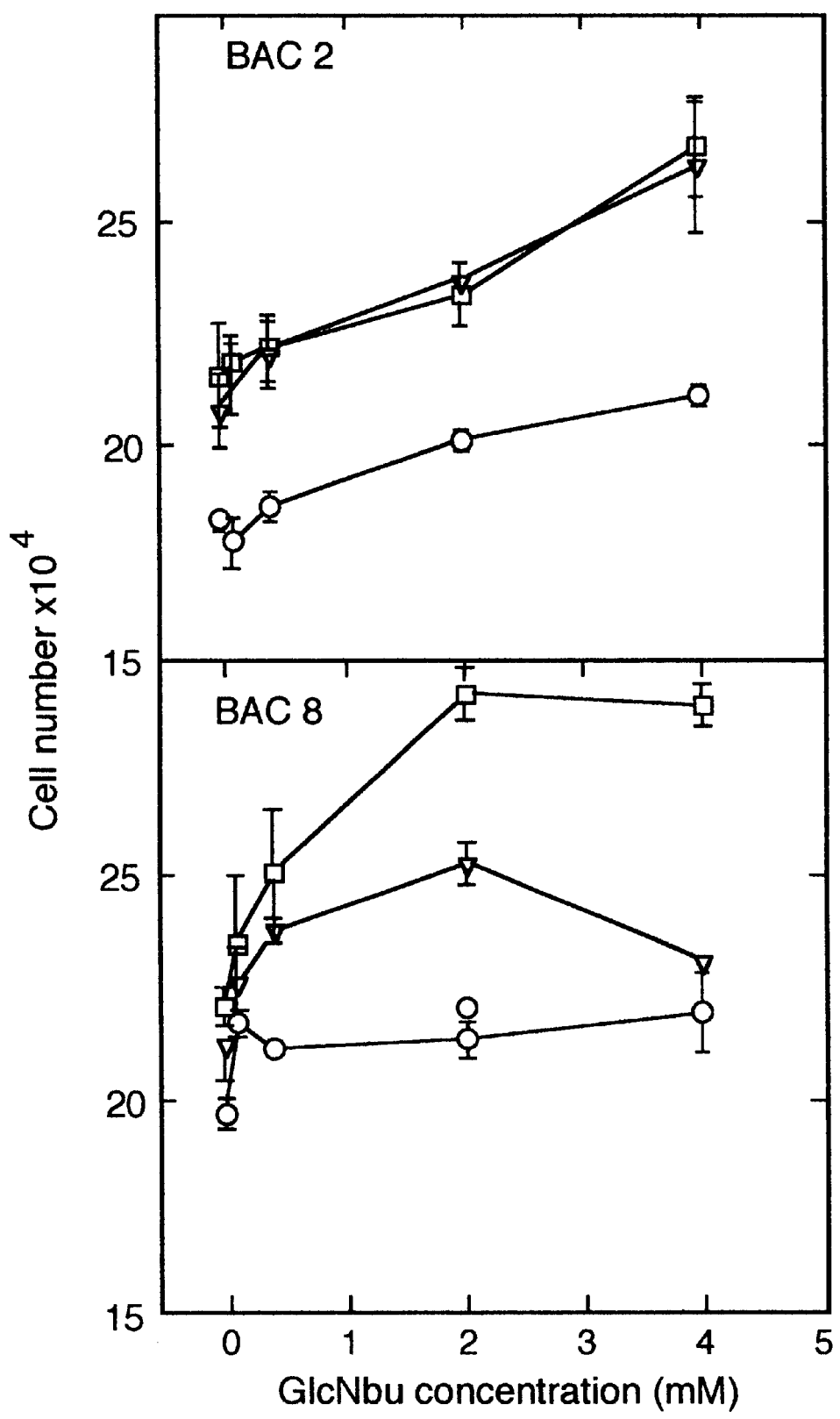
FIG. 12: This is a comparison of the effect of glucose and GlcNbu on early BAC subculture one (upper panel) and late subculture eight (lower panel). □, no glucose; ▽, 0.06 mg/ml glucose; and O, 0.125 mg/ml glucose.
Figure 13:
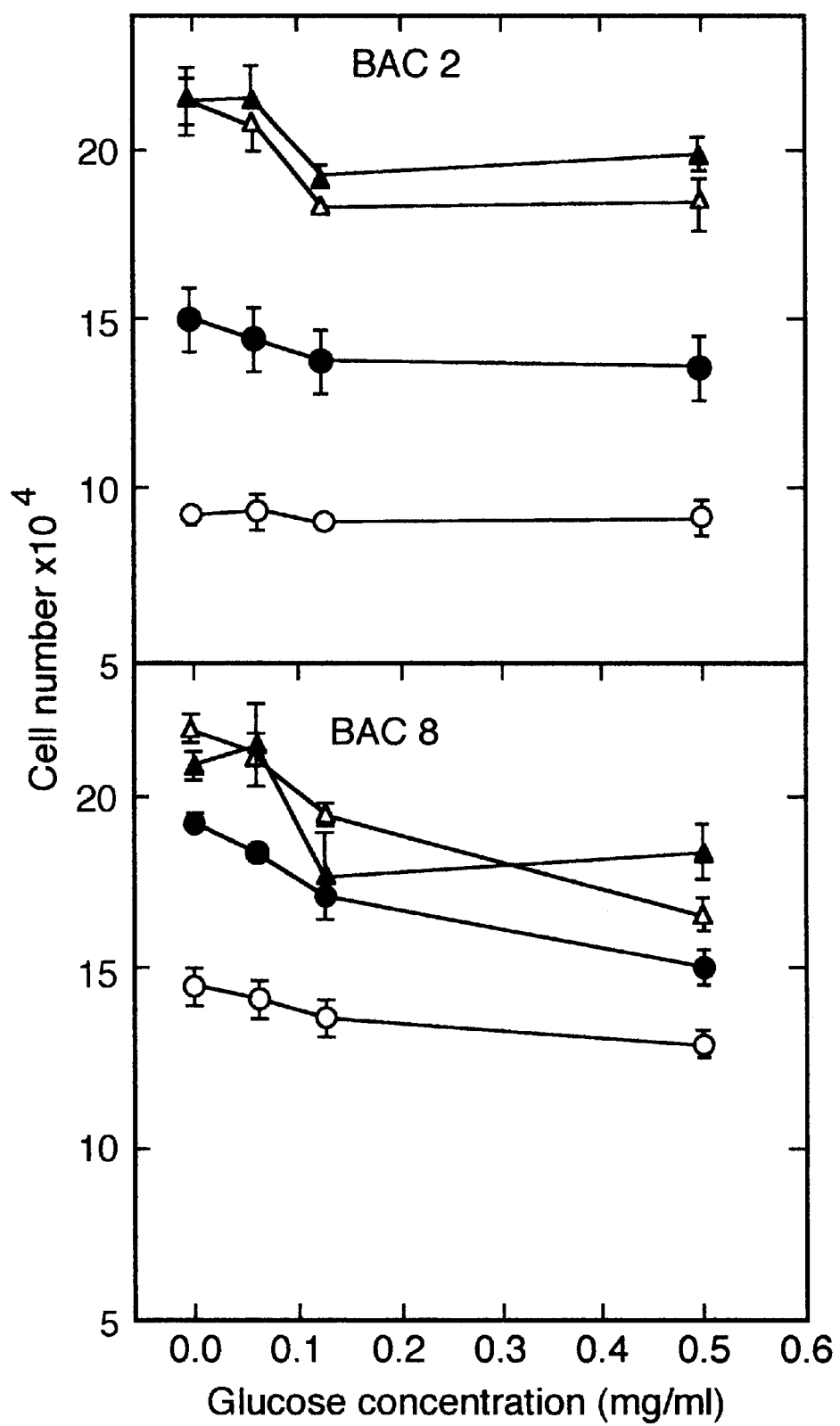
FIG. 13: This represents the effect of glucose on chondrocyte subcultures 2 and 8 cell proliferation at various time intervals. O, 4d; ●, 7d; ▽, 10d; and ▼, 14d.

Further experiments were carried out to determine whether the growth stimulation could be due to butyrate group or a mechanism solely dependent on GlcNbu. In this case, chondrocytes (BAC subculture 6) were maintained in culture in the presence of glucose (1 mg/ml), serum (20%) and various concentrations (0–6 mM) of sodium butyrate, GlcNbu and GlcN. GlcNbu increased cell growth, while GlcN and sodium butyrate decreased cell growth (FIG. 10). This suggests that GlcNbu enters the cells intact, without being metabolized to GlcN and butyrate, and there is no problem on its transport across the cell membrane. Therefore, the growth stimulation observed is due to GlcNbu. The effect of GlcNbu at varying glucose medium concentrations (0–0.5 mg/ml) were evaluated using early and late subcultured chondrocytes. GlcNbu stimulation of both early and late subcultured chondrocyte cell growth is higher in the absence of glucose or very low glucose concentration (FIGS. 11 and 12). Dose response curve for the effect of glucose on cell growth at various time intervals showed a decrease in cell number with increase in glucose concentration (FIG. 13). This suggests that chondrocytes may require little or no glucose for their metabolism, and hence may utilize other nutrients.

Further experiments were carried out to determine the effect of GlcNBu on glycosaminoglycan synthesis by Bovine Articular Chondrocytes.

Figure 14:
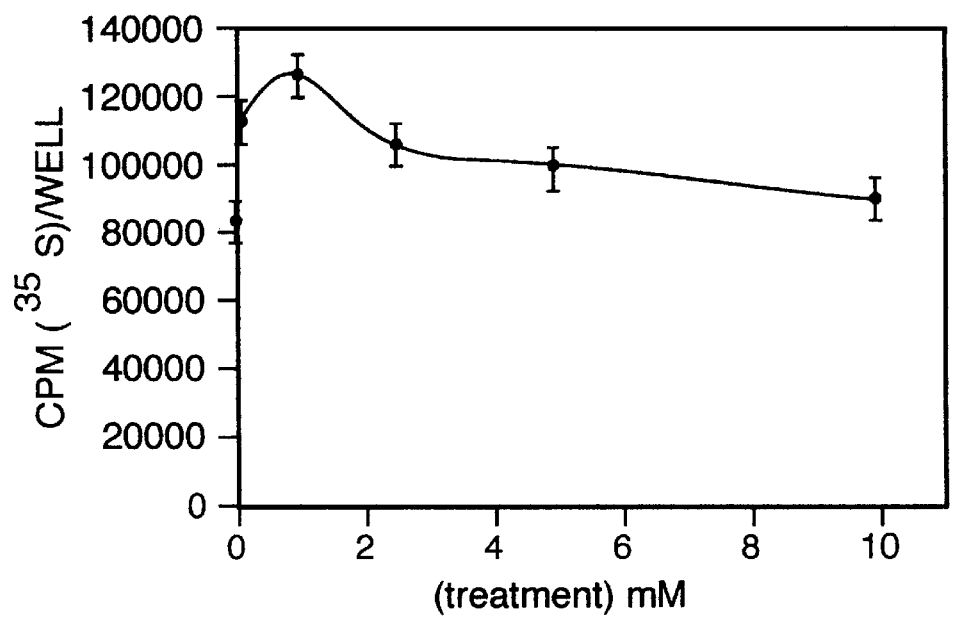
FIG. 14: Represents a graph of the effect of GlcNBu on glycosaminoglycan synthesis by Bovine Articular Chondrocytes.

Bovine articular chondrocytes were grown to confluency in 35 mm wells and labelled with $^{35}S$ for 4 days in the presence of different concentrations of GlcNBu. The Glycosaminoglycans (GAG) were isolated from the medium and the radioactivity incorporated into the isolated GAG was determined With reference to FIG. 14, the results are expressed on a per well basis and represent the means and standard deviations from four replicate wells. The vertical axis shows the amount of radioactivity incorporated into the GAG. The horizontal axis shows the concentration of GlcNBu (0.1+10 mM) for each treatment. The control (0 mM concentration of GlcNBu) is the first point on the left indicating 82,000 CPM and the lowest concentration of GlcNBu is 0.1 mM indicating 112,000 CPM.

GlcNBu Administration to Rats—Inflammatory Arthritis Model

In this study GlcNBu was compared to GlcN to determine the relative effects on an experimentally induced inflammatory arthritis in rats.

GlcNBu has the formula (II):

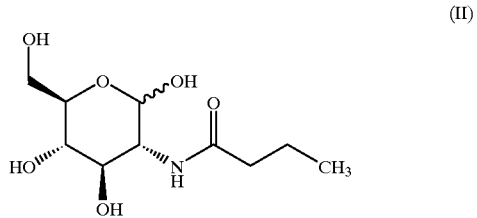

(II)

The experimental arthritis was induced by injecting cell walls of streptococcal bateria intra-peritoneally into Lewis rats. The resulting arthritis leads to cartilage and bone destruction in the injected rat. This experimental model is considered to provide some of the most useful insights in the development of human inflammatory, destructive arthropathies.

Method: Inflammatory arthritis was induced in Lewis strain rats by a single intra-peritoneal injection of the streptococcal wall pepti-polysaccharide antigen, as described in Brahn E. "Animal models of rheumatoid arthritis. Clues to etiology and treatment." Clin Orthop. 1991 Apr; (265): 42–53. Review. Van den Broek M F, van Bruggen M C, Simpson S A, Severijnen A J, van de Putte L B, van den Berg W B. "Flare-up reaction of streptococcal cell wall induced arthritis in Lewis and F344 rats: the role of T lymphocytes." Clin Exp Immunol. 1990 Feb; 79 (2): 297–306. Chen W., Jin W, Cook M, Weiner H L, Wahl S M. "Oral delivery of group A streptococcal cell walls augments circulating TGF-beta and suppresses streptococcal cell wall arthritis." J Immunol. 1998 Dec. 1; 161 (11): 6297-304. On the same day as the injection, the rats had their drinking water supplemented either with 5 mg or 50 mg of GlcN or GlcNBu in 400 ml of water. There were three rats in each of the above groups. The rats drank the water containing the above compounds in an unrestricted fashion. The drinking water was replenished, when finished, so that the rats drank the same concentrations of the compounds throughout the experimental observation period. Each animal consumed approximately between 20–30 ml of water each day for each of the groups. After 18 days of experimental observation, the rats' hind legs were visually inspected for clinical assessment of the development of arthritis.

Results: The rats herein indentified as GlcN L Oral 2 which had been treated with 5 mg GlcN in the drinking water, showed well-developed arthritis with swelling and redness in both of the hind lower legs. The rat, GlcNBu L Oral 2, the comparable animal, which had been treated with GlcNBu 5 mg showed normal hind lower legs and no clinical evidence of arthritis.

The rat identified GlcN H Oral 1, which had been treated with 50 mg of GlcN in the drinking water, showed well-developed arthritis with swelling and redness in the right lower leg and less so in the left lower leg. The rat labelled GlcNBu H Oral 1, the comparable animal which had been treated with GlcNBu 50 mg showed minimal swelling in the right lower leg and probably a normal left lower leg.

Dog Study-1

Method

1 Week administration to arthritic/dysplastic dogs @500 mg set daily dose. A Daily Journal and Video record was kept.

Subject

The subject was a 9-year-old female collie crossbreed which had osteoarthritis due to a prior left anterior cruciate ligament injury (a previous tear now repaired). The animal had a noticeable limp from the limb injury. The animal is currently medicated with glucosamine at 500 mg per day.

| Phase 1 | When glucosamine treatment was suspended, the GlcNBu, hereinafter termed MGD, was administered in a solution poured onto food in its place at 500 mg per day for a period of one week. |
| --- | --- |
| Phase 2 | After one week of MGD administration, MGD was withdrawn and the animal was observed with no additional nutraceutical (glucosamine or MGD) for a period of one week. |

For both Phase 1 and Phase 2 a video diary of a few minutes of two or three of the animal's exercise periods and a daily journal of casual observations was kept.

Journal Entry Titles Were as Follows:

1 Does general mobility/stiffness increase/decrease/or stay the same compared to glucosamine This is to assess the effectiveness of the MGD compared to glucosamine on a day to day basis.

2 Does general mobility/stiffness increase/decrease/or stay the same with each passing day This is to assess mobility and stiffness compared to the previous day, i.e. to try to pick up any cumulative effects of MGD.

3 Temperament: increase/decrease/stay the same

A general increase in temperament may be associated with a decrease in pain and/or increase in mobility and vice versa.

4 Feeding/drinking behaviour: normal/abnormal

This is to assess the palatability of the MGD to the animal.

Video Journal Entries Were Taken as Follows:

| Phase 1 | Day ## | Time | Day | Time | Day | Time |
| --- | --- | --- | --- | --- | --- | --- |
| Phase 2 | Day ## | Time | | | | |

In this one-week study of administration of MGD the MGD was tolerated at least at the same level as glucosamine. Furthermore, its protective effects appear to be at least as good as glucosamine. The daily journal completed by the owner shows no decrease in protective effects of MGD compared to glucosamine. When the MGD was discontinued in Phase 2, observation of the dog revealed a recurrence of a slight limp in the animal at Day 7 of Phase 2. This limp was "not expected" as reported by the owner and, thus, was seen as a direct result of non-medication with the MGD.

Video Evidence

Video clips from Phase 1 showed no appreciable difference from baseline (1st video clip of animal medicated with glucosamine). One video clip during Phase 1 was taken in the morning rather than early evening and the owner advised that the animal is stiff in the morning even when taking glucosamine, video evidence reflect this observation.

Video clips taken on day 7 of Phase 2 (Day 14 overall) showed a much stiffer gait and a slight limp. Owner stated that this was abnormal behaviour for her dog.

Other Observations

The MGD was palatable to the dog and no adverse reactions were observed. The dog's temperament remained calm during the study period and feeding and drinking behaviour are not altered.

Dog Study-2

Method

1 Week administration to arthritic/dysplastic dogs @ 500 mg set daily dose. Daily Journal and Video record was kept as described under Dog Study-1.

Subject

The subject was a 16-year-old female labrador crossbreed which had hip dysplasia evident in both hind limbs due to either age or an injury sustained at the age of 9 years. The animal was not currently medicated with glucosamine or other compound and had a noticeably stiff gait and restricted movement when walking.

Phase 1 The MGD was administered at 500 mg per day for a period of one week in a solution poured onto food.

As the week progressed the owner noticed several positive changes in the dog as did a neighbour who gave unsolicited positive comments about the animal. The dog appeared to be "perkier" and able to "bounce up stairs", was "more playful" and able to perform "harder movements" such as getting up, etc. Overall the owner notes "isolated examples of improvement".

Phase 2 After one week of MGD administration, MGD was withdrawn and the animal was observed with no further medication for a period of one week.

Conclusions

Anecdotal evidence from day 2 of GlcNBu administration showed a period of improvement in the dog. The owner advised of an abnormal event occurring whereby the dog appeared to be more mobile ("rejuvenated" in the owner's words) during and after a period of exercise. At Day 3 of GlcNBu treatment there was also evidence of increased protective behaviour by the animal towards property and was much more eager to follow and confront other dogs in this respect. Normal behaviour was just vocal with no real urge to follow and confront.

Although this disclosure has described and illustrated certain preferred embodiments of the invention, it is to be understood that the invention is not restricted to those particular embodiments. Rather, the invention includes all embodiments which are functional or mechanical equivalents of the specific embodiments and features that have been described and illustrated.

What is claimed is:

1. A method of treatment of arthritis in a mammal comprising administering to said mammal an effective amount of a N-acylated-2-glucosamine derivative of the general formula (I):

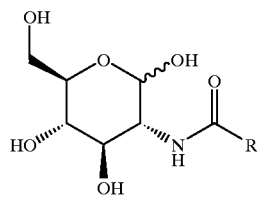
(I)

wherein R is an alkyl radical of the general formula $C_nH_{2n+1}$ wherein n is selected from 2–12; and pharmaceutically acceptable salts, esters and glucosides thereof.

2. A method of enhancing cartilage formation in a mammal comprising administering to said mammal an effective amount of a N-acylated-2-glucosamine derivative of the general formula (I):

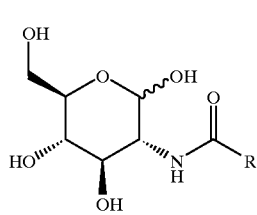
(I)

wherein R is an alkyl radical of the general formula $C_nH_{2n+1}$ wherein n is selected from 2–12; and pharmaceutically acceptable salts, esters and glucosides thereof.

3. A method of enhancing mammalian chondrocyte cell proliferation comprising treating a population of mammalian chondrocyte cells with an effective amount of a N-acylated-2-glucosamine derivative of the general formula (I):

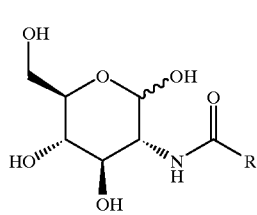
(I)

wherein R is an alkyl radical of the general formula $C_nH_{2n+1}$ wherein n is selected from 2–12; and pharmaceutically acceptable salts, esters and glucosides thereof.

4. A method of enhancing the production of glucosaminoglycan by treating mammalian chondrocytes with an effective amount of a N-acylated- 2-glycosamine of the general formula (I):

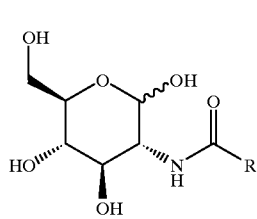
(I)

wherein R is an alkyl radical of the general formula $C_nH_{2n+1}$ wherein n is selected from 2–12; and pharmaceutically acceptable salts, esters and glucosides thereof.

5. A method for alleviating the symptoms of arthritis selected from the group consisting of joint stiffness and restricted mobility in mammal comprising administering to said mammal an effective amount of a N-acylated-2-glucosamine derivative of the general formula (I):

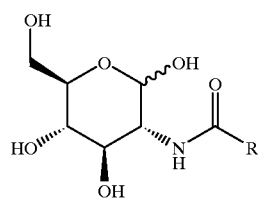
(I)

wherein R is an alkyl radical of the general formula $C_nH_{2n+1}$ wherein n is selected from 2–12; and pharmaceutically acceptable salts, esters and glucosides thereof.

6. A method as defined in claim 1 wherein said arthritis is selected from the diseases consisting of osteoarthritis, inflammatory arthritis, traumatic arthritis, degenerative arthritis and dysplastic arthritis.

7. A method as defined in claim 1 wherein said arthritis is osteoarthritis.

8. A method as defined in claim 1 wherein said arthritis is inflammatory arthritis.

9. A method as defined in claim 1 wherein n is selected from 2–5.

10. A method as defined in claim 1 wherein n is 3 and the N-acylated-2-glucosamine has the formula (II):

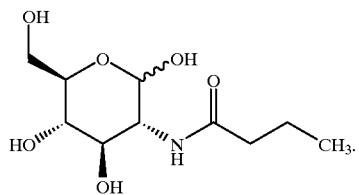
(II)

11. A N-acylated-2-glucosamine derivative of the general formula (I)

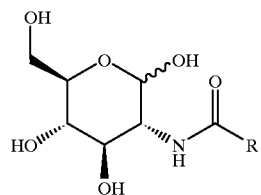
(I)

when used for a treatment in a mammal selected from the group consisting of (a) arthritis; (b) enhancing cartilage formation; (c) enhancing chondrocytes cell proliferation; (d) production of glycosaminoglycan; and (e) alleviating the symptom of joint stiffness and restricted mobility.

12. A N-acylated-2-glucosamine derivative of the general formula (II)

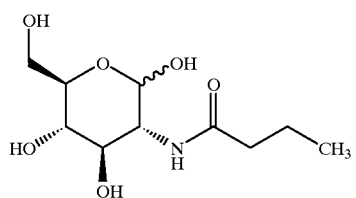
(II)

when used for a treatment in a mammal selected from the group consisting of (a) arthritis; (b) enhancing cartilage formation; (c) enhancing chondrocytes cell proliferation; (d) production of glycosaminoglycan; and (e) alleviating the symptom of joint stiffness and restricted mobility.

13. A pharmaceutical composition comprising a N-acylated-2-glucosamine derivative of the general formula (I):

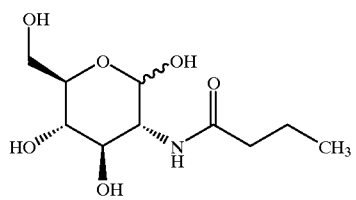
(I)

in admixture with a pharmaceutically acceptable carrier or diluent therefore when used for a treatment of a mammal selected from the group consisting of (a) arthritis; (b) enhancing cartilage formation in a mammal; (c) enhancing chondrocytes cell proliferation; (d) production of glycosaminoglycan in a mammal; and (e) alleviating the symptoms of joint stiffness and restricted mobility.

14. A pharmaceutical composition as defined in claim 13 comprising a N-acylated-2- glucosamine derivative of the formula (II):

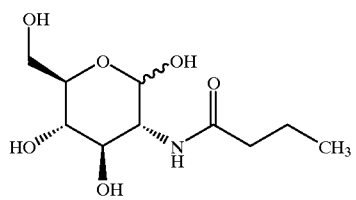
(II)

15. A process for the manufacture of a pharmaceutical composition as defined in claim 13 comprising admixing said N-acylated-2-glucosamine derivative with a pharmaceutical acceptable carrier or diluent therefore.

\* \* \* \* \*